March 17, 1959 E. S. BOERNER Plant Pat. 1,820
CHRYSANTHEMUM PLANT
Filed Aug. 21, 1958
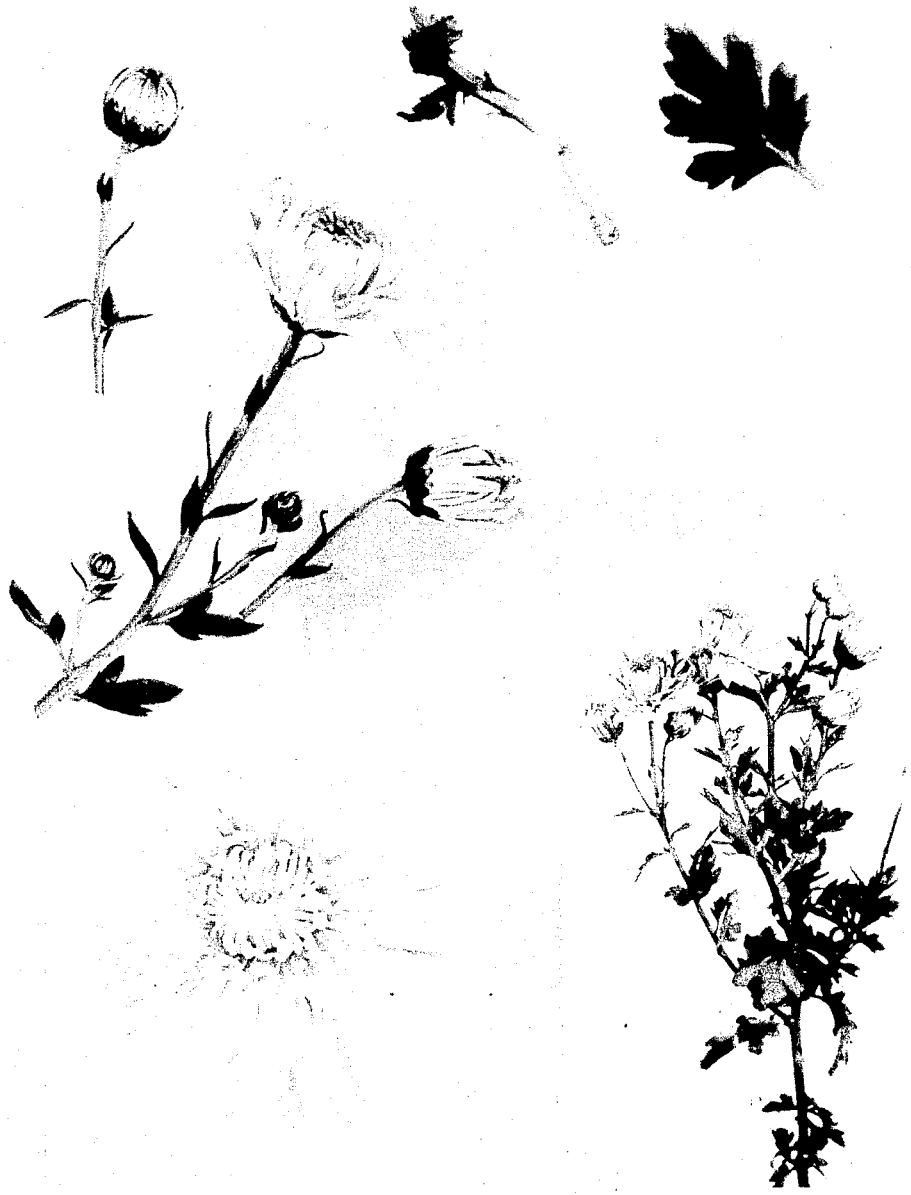
Inventor.
E. S. Boerner
By: Robb & Robb
Attorneys.

United States Patent Office

Plant Pat. 1,820
Patented Mar. 17, 1959

1,820

CHRYSANTHEMUM PLANT

Eugene S. Boerner, Newark, N. Y., assignor to Jackson & Perkins Company, Newark, N. Y., a corporation of New York Application August 21, 1958, Serial No. 756,493

1 Claim. (Cl. 47—60)

The present invention relates to a new and distinct variety of chrysanthemum plant of the shaggy decorative type, which was originated by me by crossing an unnamed and unpatented seedling of "September Dawn" (unpatented) × "Thrush" (Plant Patent No. 1,168) with the variety "Seagull" (Plant Patent No. 1,130).

The primary objective of this breeding was to produce a new chrysanthemum variety which bears flowers of a pastel pink color, combined with a large flower size and a decorative flower form which is typical of the parent variety "Seagull." This objective was fully achieved, along with other improvements, as evidenced by the following characteristics which are outstanding in the new variety and which distinguish it from its parents as well as from all other varieties of which I am aware:

(1) An early blooming habit;

(2) Large flower size and shaggy decorative form of the flowers;

(3) Soft petal texture; and (4) A distinctive La France Pink general color tonality of the flowers.

Asexual reproduction of the new variety by both top cuttings and underground runners, as performed at Newark, New York, shows that these characteristics and distinctions come true to form and are established and transmitted through succeeding propagations.

The accompanying drawings shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, in the early morning in the early part of October:

Parentage: An unnamed seedling of "September Dawn" × "Thrush" × "Seagull."

Classification: Shaggy decorative.

Growth: Vigorous; attains a height of 24 inches.

Cold resistance: The plant is winter hardy in northern New York; flowers burn lightly with early frost.

Blooming period: In the Newark, New York climatic area, average date of start of bloom is early September, with bloom continuing until frost.

*Flower*

Bud:

*Color.*—When sepals first divide—Deep Rose Pink, Plate 12. When petals begin to unfurl—Venetian Pink, Plate 13. When half-blown: inside of petals—La France Pink, Plate 1; outside of petals—Hermosa Pink, Plate 1, lightly overcast with Thulite Pink, Plate 26.

*Peduncle.*—Color—Pois Green, Plate 41. Strength—medium.

Bloom:

*Size.*—From 5 inches to 5½ inches.

*Stem.*—Medium; normal.

*Form.*—Shaggy decorative.

*Petalage.*—Semi-double.

*Color.*—Center of flower—La France Pink, Plate 1, lightly overcast with Eosine Pink, Plate 1 in the lower half of the petal. Outer petals—Hermosa Pink, Plate 1. Base of petals—Chartreuse Yellow, Plate 31. Inside of petals—La France Pink, Plate 1. Reverse of petals—white, lightly overcast with Cameo Pink, Plate 26.

*Petals.*—Texture—soft. Form—long; pointed.

*Fragrance.*—Characteristic chrysanthemum.

*Plant*

Form: Upright.

Growth: Airy.

Foliage:

*Size.*—Medium.

*Quantity.*—Few leaves on upper part of stem.

*Color.*—Upper side—Dark Dull Yellow-Green, Plate 32. Reverse side—Bice Green, Plate 27.

*Texture.*—Leathery.

I claim:

A new and distinct variety of chrysanthemum plant of the shaggy decorative type, substantially as herein shown and described, characterized particularly as to novelty by the unique combination of an early blooming habit, large flower size, soft petal texture, and a distinctive La France Pink general color tonality of the flowers.

No references cited.